US00PP34504P3

(12) United States Plant Patent
Post

(10) Patent No.: US PP34,504 P3
(45) Date of Patent: Aug. 16, 2022

(54) ***CHRYSANTHEMUM* PLANT NAMED 'DLFEVID1'**

(50) Latin Name: ***Chrysanthemum* X *morifolium***
Varietal Denomination: DLFEVID1

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/502,537

(22) Filed: Oct. 15, 2021

(65) Prior Publication Data

US 2022/0124952 P1 Apr. 21, 2022

Related U.S. Application Data

(60) Provisional application No. 63/093,198, filed on Oct. 17, 2020.

(51) Int. Cl.
*A01H 5/02* (2018.01)
*A01H 6/14* (2018.01)

(52) U.S. Cl.
USPC ..... Plt./288
CPC ..... *A01H 6/1424* (2018.05)

(58) Field of Classification Search
USPC ..... Plt./288
CPC ..... A01H 5/02
See application file for complete search history.

(56) References Cited

PUBLICATIONS https://online.plantvarieties.eu/publicConsultationDetails?registerId=20201582&denomination=DLFEVID1; Mar. 16, 2022; 3 pages.*

* cited by examiner

*Primary Examiner* — Kent L Bell
(74) *Attorney, Agent, or Firm* — C. Anne Whealy

(57) ABSTRACT

A new and distinct cultivar of *Chrysanthemum* plant named 'DLFEVID1', characterized by its upright plant habit; uniform growth habit; dark green-colored leaves; uniform flowering habit; strong upright flowering stems; dense pompon-type inflorescences with numerous white-colored ray florets; relative tolerance to high and low production temperatures; resistance to *Fusarium* and White Rust; and good postproduction longevity.

1 Drawing Sheet

Figure 1:
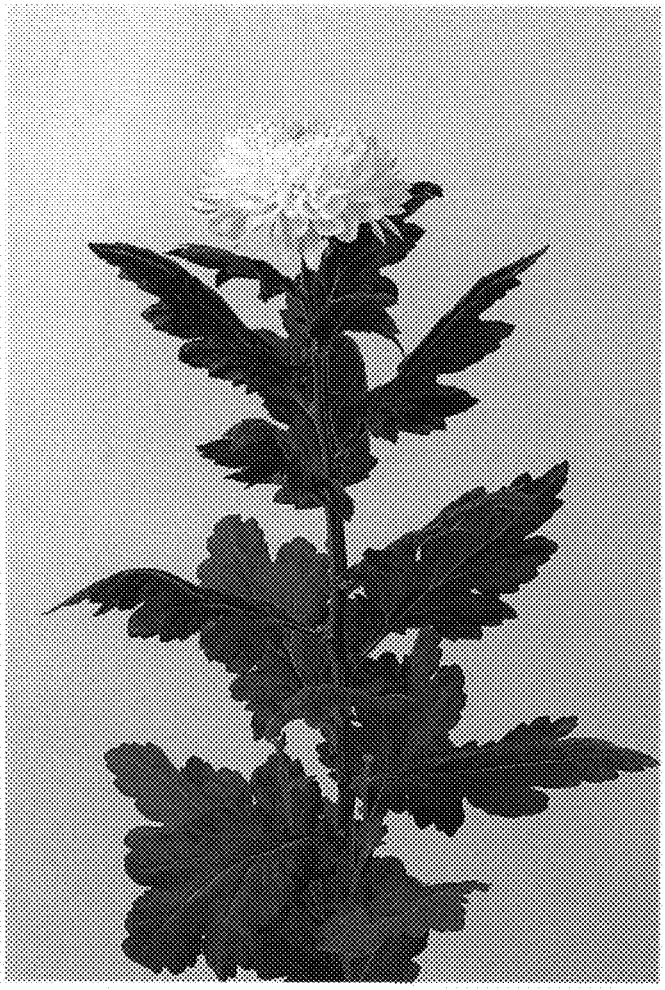

Botanical designation: *Chrysanthemum* X *morifolium*.
Cultivar denomination: 'DLFEVID1'.

STATEMENT REGARDING PRIOR DISCLOSURES BY INVENTOR/APPLICANT & ASSIGNEE

An European Plant Breeders' Rights application for the instant plant was filed by the Assignee, Deliflor Royalties B.V. of Maasdijk, The Netherlands on Jun. 25, 2020, application number 2020/1582. Foreign priority is not claimed to this application.

A Colombian Plant Breeders' Rights application for the instant plant was filed by the Assignee, Deliflor Royalties B.V. of Maasdijk, The Netherlands on Dec. 12, 2020, application number A202732. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFEVID1'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in November, 2016 of a proprietary selection of *Chrysanthemum* x *morifolium* identified as code number DB 49894, not patented, as the female, or seed, parent with a proprietary selection of *Chrysanthemum* x *morifolium* identified as code number DB 58765, not patented, as the male, or pollen, parent. The new *Chrysanthemum* plant was discovered and selected as a single flowering plant from within the progeny of the stated cross-pollination in a controlled greenhouse environment in Maasdijk, The Netherlands in September, 2017.

Asexual reproduction of the new *Chrysanthemum* plant by vegetative terminal cuttings since September, 2017 in a controlled greenhouse environment in Maasdijk, The Netherlands, has shown that the unique features of this new

*Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFEVID1'. These characteristics in combination distinguish 'DLFEVID1' as a new and distinct *Chrysanthemum* plant:

1. Upright plant habit; uniform growth habit.
2. Dark green-colored leaves.
3. Uniform flowering habit.
4. Strong upright flowering stems.
5. Dense pompon-type inflorescences with numerous white-colored ray florets.
6. Relatively tolerant to high and low production temperatures.
7. Resistant to *Fusarium* (*Fusarium oxysporum*) and White Rust (*Puccinia horiana*).
8. Good postproduction longevity.

Plants of the new *Chrysanthemum* differ primarily from plants of the female parent selection in inflorescence size as plants of the new *Chrysanthemum* have larger inflorescences than plants of the female parent selection. In addition, plants of the new *Chrysanthemum* have slightly lighter green-colored leaves than plants of the female parent selection.

Plants of the new *Chrysanthemum* differ primarily from plants of the male parent selection in inflorescence type as plants of the new *Chrysanthemum* have pompon-type inflorescences whereas plants of the male parent have incurved-type inflorescences. In addition, leaves of plants of the new *Chrysanthemum* have fewer leaf margin indentations than leaves of plants of the male parent selection.

Plants of the new *Chrysanthemum* can also be compared to plants of *Chrysanthemum* X *morifolium* 'DLFSIB1', not patented. In side-by-side comparisons, plants of the new *Chrysanthemum* differ primarily from plants of 'DLFSIB1' in the following characteristics:

1. Plants of the new *Chrysanthemum* have larger inflorescences than plants of 'DLFSIB1'.
2. Ray florets of plants of the new *Chrysanthemum* have obtuse to emarginate apices whereas ray florets of plants of 'DLFSIB1' have rounded apices.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph at the top of the sheet (FIG. 1) comprises a side perspective view of a typical flowering stem of 'DLFEVID1' grown as a disbud-type cut flower.

Figure 2:
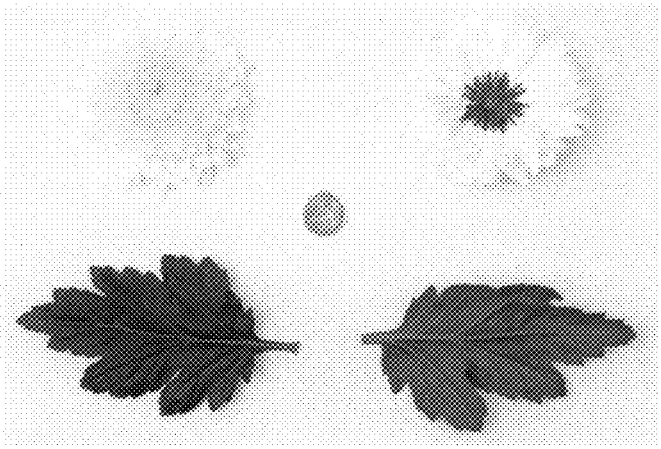

The photograph at the bottom of the sheet (FIG. 2) is a close-up view of upper (left) and lower (right) surfaces of typical inflorescences (top of figure) and typical leaves (bottom of figure) of 'DLFEVID1'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem disbud-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFEVID1'.

Parentage:

*Female, or seed, parent*.—Proprietary selection of *Chrysanthemum* x *morifolium* identified as code number DB 49894, not patented.

*Male, or pollen, parent*.—Proprietary selection of *Chrysanthemum* x *morifolium* identified as code number DB 58765, not patented.

Propagation:

*Type*.—Terminal vegetative cuttings.

*Time to initiate roots, summer*.—About four days at temperatures about 20° C.

*Time to initiate roots, winter*.—About six days at temperatures about 20° C.

*Time to produce a rooted young plant, summer*.—About 13 days at temperatures about 20° C.

*Time to produce a rooted young plant, winter*.—About 15 days at temperatures about 20° C.

*Root description*.—Fine, fibrous; typically light brown in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous decorative-type cut flower that is typically grown as a single stem disbud-type; upright plant habit; vigorous growth habit and rapid growth rate.

*Plant height, soil level to top of foliar plane*.—About 62.1 cm.

*Plant height, soil level to top of inflorescence plane*.—About 66.6 cm.

*Plant diameter*.—About 21.6 cm.

*Flowering stem length*.—About 59.4 cm.

*Flowering stem diameter*.—About 7 mm.

*Flowering stem internode length*.—About 2.2 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 138B.

*Flowering stem color, developed*.—Close to 146A and 146C.

*Leaf description*.—Arrangement: Alternate; simple. Length: About 12.7 cm. Width: About 8.4 cm. Shape, in overall outline: Ovate to oblong. Apex: Abruptly acute, minute. Base: Attenuate. Margin: Palmately lobed, coarsely crenate to dentate to crenate to serrate; sinuses parallel, convergent and divergent and shallow to medium in depth. Texture and luster, upper surface: Moderately to densely pubescent, not rugose; moderately velvety; slightly glossy. Texture and luster, lower surface: Moderately to densely pubescent, prominent venation; slightly velvety; matte to slightly glossy. Venation pattern: Pinnate, reticulate. Color: Developing leaves, upper surface: Close to 137A. Developing leaves, lower surface: Close to 138B. Fully developed leaves, upper surface: Close to darker than 139A; venation, close to 147B. Fully developed leaves, lower surface: Close to between NN137C and 147B; venation, close to 146D. Petioles: Length: About 1.2 cm. Diameter: About 4 mm by 4 mm. Strength: Moderately strong. Texture and luster, upper and lower surfaces: Densely pubescent; slightly glossy. Color, upper surface: Close to 148B; edges, close to 137A. Color, lower surface: Close to 147B; edges, close to between 137C and 143A. Stipules: Quantity, appearance and arrangement: Two leafy stipules, opposite, at the petiole attachment to the stem. Length: About 1.1 cm. Width: About 1.1 mm. Shape, in overall outline: Roughly obovate to reniform with emarginate apices. Texture and luster, upper surface: Moderately to densely pubescent; slightly glossy. Texture and luster, lower surface: Moderately to densely pubescent; matte to slightly glossy. Color, upper surface: Close to 147B. Color, lower surface: Close to between NN137C and 147B.

Inflorescence description:

*Appearance*.—Dense pompon-type inflorescence form with narrowly oblanceolate-shaped ray florets and tubular disc florets; inflorescences borne perpendicular to peduncles and face mostly upright; ray and disc florets develop acropetally on a capitulum; typically grown as a disbud-type, but can also be grown as a spray-type.

*Fragrance*.—Faintly fragrant; typical of *Chrysanthemums*.

*Flowering response*.—Under natural conditions, plants flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 59 days later when grown as a disbud-type.

*Postproduction longevity*.—Good postproduction longevity; after a seven-day storage period, cut flowers will maintain good color and substance for about two weeks in an interior environment; inflorescences persistent.

*Quantity of inflorescences*.—Typically grown as a disbud-type, however, when grown as a spray-type, about 27 inflorescences develop per flowering stem.

*Inflorescence size*.—Diameter, grown as a disbud-type: About 9 cm. Depth (height), grown as a disbud-type: About 7.4 cm. Disc diameter, grown as a disbud-type: About 6 mm; inconspicuous. Diameter, grown as a spray-type: About 7.7 cm. Depth (height), grown as a spray-type: About 4 cm. Disc diameter, grown as a spray-type: About 4 mm; inconspicuous.

*Receptacles*.—Height, grown as a disbud-type: About 5 mm. Diameter, grown as a disbud-type: About 1.1 cm. Height, grown as a spray-type: About 4 mm. Diameter, grown as a spray-type: About 8 mm. Shape: Flattened globular. Color: Close to 145C to 145D.

*Inflorescence buds*.—Height: About 1.1 cm. Diameter: About 1.2 cm. Shape: Flattened spherical to close to spherical. Texture and luster: Distally, smooth and glabrous; proximally, moderately pubescent; slightly glossy. Color: Developing involucral bracts, close to 137B and 138C; developing ray florets, close to between 155C and NN155C.

*Ray florets*.—Quantity and arrangement: About 480 arranged in about twelve whorls. Length, when grown as a disbud-type: About 3.4 cm; varying between 2 cm and 4.2 cm. Width, when grown as a disbud-type: About 1.2 cm; varying between 0.4 cm and 1.5 cm. Length, when grown as a spray-type: About 2.7 cm; varying between 0.7 cm and 4 cm. Width, when grown as a spray-type: About 9 mm; varying between 0.1 cm and 1.5 cm. Shape: Narrowly oblanceolate; slightly concave, slightly carinate. Apex: Obtuse to emarginate. Base: Long and narrowly cuneate. Margin: Entire; coarsely undulate. Aspect: About 65° from vertical. Texture and luster, upper surface: Smooth, glabrous; moderately velvety; matte. Texture and luster, lower surface: Smooth, glabrous; slightly velvety; slightly glossy. Color: When opening, upper surface: Close to NN155D. When opening, lower surface: Close to NN155C. Fully opened, upper and lower surfaces: Close to NN155D; at the base, close to 151D; venation, similar to lamina colors; colors do not change with subsequent development.

*Disc florets*.—Quantity and arrangement: About 45 at the center of the receptacle. Length: About 7 mm. Diameter: About 2 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Apex: Close to 13A. Distally: Close to 11A. Proximally: Close to between 145D and 150D. Color, fully opened, inner and outer surfaces: Apex: Close to 9A. Distally: Close to 145C. Proximally: Close to 145D.

*Involucral bracts*.—Quantity and arrangement: About 30 arranged in about two whorls. Length: About 1.3 cm. Width: About 4 mm. Shape: Narrowly ovate. Apex: Narrowly obtuse. Base: Cuneate. Margin: Entire. Texture and luster, upper surface: Smooth, glabrous; glossy. Texture and luster, lower surface: Moderately pubescent; matte. Color, upper surface: Close to 137C; lateral margins, translucent and close to 156C to 156D and apical margins tinged with close to N199A. Color, lower surface: Close to 137A; lateral margins, translucent and close to 156C to 156D and apical margins tinged with close to N199A.

*Peduncles*.—Length, terminal peduncle: About 3.9 cm. Diameter, terminal peduncle: About 6 mm. Length, third peduncle: About 6.5 cm. Diameter, third peduncle: About 3 mm. Strength: Strong. Aspect, terminal peduncle: Upright. Aspect, third peduncle: About 45° from the flowering stem axis. Texture and luster: Moderately pubescent; slightly glossy. Color: Close to 137C and 138B.

*Reproductive organs*.—Androecium: Present on disc florets only. Quantity: About five per floret. Filament length: About 2 mm. Filament color: Close to 145D. Anther size: About 0.5 mm by 2 mm. Anther shape: Oblong. Anther color: Close to 154D. Pollen amount: Moderate. Pollen color: Close to 17A. Gynoecium: Present on both ray and disc florets. Quantity: One per floret. Pistil length: About 7 mm. Style length: About 6 mm. Style color: Close to 3C. Stigma diameter: About 1 mm. Stigma shape: Cleft to three-parted, decurrent. Stigma color: Close to 12A. Ovary color: Close to 157A.

*Seeds and fruits*.—To date, seed and fruit production have not been observed on plants of the new *Chrysanthemum*.

Pathogen & pest resistance: Plants of the new *Chrysanthemum* have been observed to be resistant to *Fusarium* (*Fusarium oxysporum*) and White Rust (*Puccinia horiana* (strains PhNL1 and PhBE6)). To date, plants of the new *Chrysanthemum* have not been observed to be resistant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFEVID1' as illustrated and described.

* * * * *